United States Patent [19]

Drummond et al.

[11] 4,110,542

[45] Aug. 29, 1978

[54] PREPARATION OF DIHYDROXYDIPHENYL ALKANES

[75] Inventors: James C. Drummond, Bridgeton; Lawrence J. Hughes, St. Charles, both of Mo.

[73] Assignee: Monsanto Company, St. Louis, Mo.

[21] Appl. No.: 755,706

[22] Filed: Dec. 30, 1976

[51] Int. Cl.$^2$ .................. C07C 37/18; C07C 39/16
[52] U.S. Cl. .................................................. 568/729
[58] Field of Search ............ 260/619 B, 621R, 624 C

[56] References Cited

U.S. PATENT DOCUMENTS

| | | | |
|---|---|---|---|
| 3,280,201 | 10/1966 | Hamilton et al. | 260/624 C |
| 3,426,358 | 2/1969 | Schlichting et al. | 260/619 B |
| 3,463,824 | 8/1969 | Velling | 260/624 C |
| 3,790,641 | 2/1974 | Oshuma et al. | 260/621 R |
| 3,857,899 | 12/1974 | Tasaka et al. | 260/624 C |

FOREIGN PATENT DOCUMENTS 46-8691  5/1971  Japan .................................. 260/624 C

OTHER PUBLICATIONS

Vestn. Khar'kov, "Politekh. Inst.," 1971, No. 60, 61–64.

*Primary Examiner*—Norman Morgenstern
*Attorney, Agent, or Firm*—James C. Bolding; Elizabeth F. Sporar

[57] ABSTRACT

A process is described for preparing 4,4'-dihydroxydiphenylethane by reacting phenol with a 1,2-dihaloethane in which the halogen is chlorine, bromine or iodine, in at least the stoichiometric proportions of 2:1 in contact with a catalyst comprising lanthanum oxide supported on an inorganic material such as silica at a temperature from about 125° to about 225° C and in the presence of a hydrogen halide as a promoter.

9 Claims, No Drawings

PREPARATION OF DIHYDROXYDIPHENYL ALKANES

BACKGROUND OF THE INVENTION

The present invention relates to the preparation of dihydroxydiphenyl alkanes by the reaction of phenol and dihaloalkanes. More particularly, it relates to a novel catalyst for the preparation of 4,4'-dihydroxydiphenylethane sometimes referred to as bisphenol E.

Dihydroxydiphenyl alkanes, also known as bisphenols, are useful in the production of high polymers, epoxy resins and high-molecular weight thermoplastic condensates as well as intermediates in organic syntheses, the best known of such compounds, bisphenol A, being widely employed. It has been suggested in an article by I. M. Nosalevich et al entitled "Preparation of dihydroxydiphenylalkanes by the alkylation of phenol by dihaloalkanes" (Vestn. Khar'kov. Politekh. Inst. 1971, No. 60, 61–4) that an increase in the number of technically available dihydroxydiphenyl alkanes would open up possibilities for modification of polymeric materials formed from them. Following this line, these workers have described several methods of preparing dihydroxydiphenyl alkanes among which is that of the direct interaction of phenol with dichloroethane or dibromoethane in the presence of zinc to give the 1,2-bis(4-hydroxyphenyl)ethane (also known as 4,4'-dihydroxydiphenylethane) and its isomers. We have now discovered that the yield of the desired isomer can be significantly increased by employing a lanthanum catalyst free of zinc.

SUMMARY OF THE INVENTION

According to the invention, phenol is alkylated with a 1,2-dihaloethane in which the halogen is chlorine, bromine or iodine in a least the stoichiometric molar proportions of 2:1 in contact with a catalyst comprising lanthanum oxide on a support such as silica at a temperature from about 125° to about 225° C. employing a hydrogen halide as promoter for the reaction to produce 4,4'-dihydroxydiphenylethane.

DESCRIPTION OF THE PREFERRED EMBODIMENTS

The process of the invention is conveniently carried out in an apparatus of the type suitable for carrying out chemical reactions in the liquid phase using a solid catalyst, i.e., a slurry-type reactor, or the liquid reactants can be pumped through a fixed bed of the catalyst. The reaction may be conducted as a batch or continuous operation. The catalyst for the reaction comprises lanthanum oxide ($La_2O_3$) on a support. Suitable support materials include silica, alumina, silica-alumina, silicates, magnesia, kaolin, Portland cement and the like with silica being the preferred support. The lanthanum oxide is present in an amount from about 5 to 80% by weight of the total catalyst and preferably represents from about 50 to about 65% by weight. The catalysts can be readily prepared in several ways. One method involves dissolving a salt of the metal such as La($NO_3$)$_2$, La $Cl_3$, etc. in water and adding the support material with stirring, heating the mixture to evaporate the water, drying and calcining. In another method of preparation, the lanthanum oxide and the support material both in powdered form can be intimately mixed before forming a paste of them with water and further mixing said paste. The paste can be spread and dried in air, after which it can be calcined in air. The calcined product can then be crushed and sieved to the desired mesh size. In still another method of preparation, the metal oxide and support material can be mixed dry together with a material which facilitates forming the mixture into pellets and then the resulting mass formed into pellets which are calcined prior to use. Calcining temperatures may vary from 300° to 1200° C. with temperatures from about 500° to about 750° C. preferred, regardless of the method by which the catalyst is prepared.

Reactant mole ratios of phenol to dihaloethane employed are at least the stoichiometric ratio of 2:1 but may be as high as 10:1 Preferably phenol-dihaloethane mole ratios in the range from 2:1 to 4:1 are employed.

As mentioned above, the reaction can be conducted at any temperature in the range from about 125° to about 225° C., Preferred reaction temperatures, however, are those from about 150° to about 185° C. Atmospheric pressure is preferred but the reaction can be conducted at superatmospheric pressures if desired.

The reaction is promoted by the presence of a hydrogen halide such as hydrogen iodide (HI) or hydrogen bromide (HBr) in the reaction system with HBr being the preferred promoter. Generally, the amount of promoter required will vary from about 0.1 to about 5.0% by weight of the dihaloethane reactant.

The 4,4'-dihydroxydiphenylethane can be recovered from the reaction mixture by conventional techniques. One procedure which can be employed to isolate this chemical involves first filtering the reaction mixture to remove the solid catalyst and then evaporating the excess phenol and unreacted dihaloethane from the filtrate under vacuum. An amount by weight equal to the residue of a solvent such as dichloreothane can then be added to residue to effect crystallization of the product. The crystalline product can be purified by continued recrystallization with an acetic acid-water mixture, a mixture of alcohols, dichlorethane or other suitable solvent to the desired purity.

The invention is illustrated in the following examples which, however are not intended to limit its scope in any manner whatsoever. For example, 1,2-dichloroethane or 1,2-diiodoethane can be substituted for the 1,2-dibromoethane shown therein.

EXAMPLE I

A catalyst containing 65% lanthanum oxide on silica was prepared by dissolving 78g of lanthanum nitrate in water and adding to the solution with stirring 78.92g of a silica sol marketed by duPont under the trademark "Ludox As - 40" which contains 40% by weight of $SiO_2$. The mixture was heated until it formed a gel-like substance. The gel was dried at a temperature of 200° C. in a drying oven after which it was ground and calcined at 500° C.

About 2.4g of the catalyst prepared as described above was charged to a tube provided with inlet and outlet means together with 5.64g of a 2:1 molar mixture of phenol and 1,2 dibromoethane (DBE). The resulting mixture was heated at a temperature of about 174° C. while hydrogen bromide (HBr) was bubbled through it over a period of about 70 minutes. Samples of the reaction effluent were taken at 20-, 50- and 70- minute intervals, respectively, and analyzed by gas chromatographic means. Portions of the samples were acetylated by heating them at 100° C. with an excess of acetic anhydride. The acetylated product was the analyzed by gas chromatographic techniques to determine the isomoerdistribution of the dihydroxydiphenylethanes (DDE'S) produced. The results are presented in Table I below.

Table I

| Sample No | Non-Acetylated Products (Wt.%) | | | | Acetylated DDE'S (Wt.%) | | | | |
|---|---|---|---|---|---|---|---|---|---|
| | DBE | Phenol | DDE'S | Intermediates | 2,2'- | 2,3'- | 2,4'- | 3,4'- | 4,4'- |
| 1 | 23.4 | 64.1 | 11 | 1.6 | 13.8 | 0.3 | 45.5 | 2.5 | 37.9 |
| 2 | 17.1 | 67.8 | 13.2 | 1.9 | 13.8 | 0.9 | 45.3 | 3.1 | 37.0 |
| 3 | 3.9 | 75.1 | 18.9 | 2.1 | 13.8 | 1.1 | 44.9 | 3.5 | 36.7 |

In runs wherein phenol and DBE in a 4:1 molar ratio were reacted at a temperature from about 140° to about 175° C. and a pressure of one atmosphere in contact with zinc bromide or zinc chloride as catalyst over reaction periods from about 3 to about 6 hours, the typical isomer distribution in the dihydroxydiphenylethane product obtained was as follows:

| Isomer | Wt% |
|---|---|
| 2,2'- | 30 |
| 2,3'- | 6 |
| 2,4'- | 40 |
| 3,4'- | 9 |
| 4,4'- | 15 |

It will be seen by comparing these results with those in Table I that a significantly higher amount of the 4,4'-dihydroxydiphenylethane is produced using the lanthanum oxide-on-silica catalyst of the present invention than can be obtained with the zinc-containing catalyst of the prior art. The lanthanum oxide catalyst is low in isomerization acitivity based on the low levels of 2,3'- and 3,4'- isomers found.

EXAMPLE 2

A catalyst was prepared essentially as described in Example I containing 65% lanthanum oxide on silica except that calcination was carried out at 1000° C.

The reaction was conducted by charging 11.75g of the catalyst described above and 56.4g of a 4:1 molar mixture of phenol and DBE and heating to about 164° C. HBr was bubbled into the flask for approximately the first 2.5 hours, then discontinued for approximately the next 3 hours, again added for about 40 minutes, discontinued for the next 5 hours and added again for the duration of the run which lasted for about one more hour. Approximately half-way through the run, an additional 11.0g of catalyst was introduced into the flask.

Samples were taken at the time intervals indicated above throughout the approximately 13-hour reaction period, numbered sequentially and analyzed by gas chromatographic means. Portions of these samples were acetylated as in Example I and the acetylated products were also analyzed using the gas chromatograph. Results of the analyses are presented in Table 2 below.

Table 2

| Sample No | Non-Acetylated Product (Wt.%) | | | | Acetylated DDE'S (Wt.%) | | | | |
|---|---|---|---|---|---|---|---|---|---|
| | DBE | Phenol | DDE'S | Intermediates | 2,2'- | 2,3'- | 2,4'- | 3,4'- | 4,4'- |
| 1 | 25.5 | 77.2 | — | 0.3 | | | | | |
| 2 | 26.6 | 73.0 | Tr | 0.4 | | | | | |
| 3 | 16 | 81.6 | 1.4 | 1.0 | 13.1 | Tr | 49.7 | 4.2 | 33 |
| 4 | 20.9 | 75.1 | 2.7 | 1.3 | 13.5 | Tr | 53.1 | 6.3 | 27.1 |
| 5 | 20.0 | 77.1 | 1.6 | 1.3 | 16.4 | Tr | 51.5 | 6.3 | 25.8 |

EXAMPLE 3

In a run similar to Example I, using the same catalyst as described in that example, the reaction tube was charged with 2.4g of catalyst and 11.3g of a 2:1 molar mixture of phenol and DBE and heated to a temperature from about 174° to 179° C. over a period of about 6 hours while HBr was bubbled slowly into the reaction mixture. An increase in the rate of addition of HBr was effected during the last hour of the reaction period. Samples of the reaction product were analyzed periodically as in Example I and portions of the product samples were also acetylated as in that example to identify the isomers by gas chromatographic means. Results of the analyses which are presented below in Table 3 show significantly increased production of the DDE'S in samples 6 and 7 which were taken after the rate of HBr addition was increased.

Table 3

| Sample No | Non-Acetylated Product (Wt.%) | | | | Acetylated Product (Wt.%) | | | | |
|---|---|---|---|---|---|---|---|---|---|
| | DBE | Phenol | DDE'S | Intermediates | 2,2'- | 2,3'- | 2,4'- | 3,4'- | 4,4'- |
| 1 | 49.6 | 48.8 | 0.97 | 0.56 | 13.3 | — | 48.8 | 2.1 | 35.9 |
| 2 | 48.1 | 49.3 | 1.8 | 0.83 | 12.7 | — | 47.3 | 2.3 | 37.7 |
| 3 | 43.3 | 52.9 | 2.6 | 1.1 | 13. | 0.4 | 45.1 | 3.4 | 37.7 |
| 4 | 38.9 | 56.7 | 3.1 | 1.3 | 13. | Tr | 45.9 | 3.6 | 37.5 |
| 5 | 33. | 63. | 2.6 | 1.4 | 14.1 | 0.4 | 45.1 | 3.9 | 36.6 |
| 6 | 4.7 | 85.8 | 7.2 | 2.3 | 13.9 | — | 46.3 | 3.9 | 35.9 |
| 7 | 0.4 | 89.2 | 8.2 | 2.2 | 16.2 | 1 | 45.8 | 3.6 | 33.5 |

What is claimed is:

1. The process for producing 4,4'-dihydroxydiphenylethane which comprises alkylating phenol with a 1,2-dihaloethane in which the halogen is chlorine, bromine, or iodine in at least the stoichiometric proportions of 2:1 in contact with a catalyst comprising lanthanum oxide supported on an inorganic material at a temperature from about 125° to about 225° C. in the presence of a hydrogen halide selected from the group consisting of hydrogen bromide and hydrogen iodide as promoter for the reaction.

2. The process of claim 1 wherein said inorganic material is selected from the group consisting of silica, alumina, silica-alumina, silicates, magnesia, kaolin and Portland cement.

3. The process of claim 2 wherein said lanthanum oxide is present in an amount from about 5 to about 80% be weight of the total catalyst.

4. The process of claim 2 wherein said inorganic support material is silica.

5. The process of claim 4 wherein said lanthanum oxide is present in an amount from about 50 to about 65% by weight of the total catalyst.

6. The process of claim 5 wherein the mole ratio of phenol to dihaloethane is in the range from about 2:1 to about 4:1.

7. The process of claim 6 wherein the temperature is in the range from about 150° to 185° C.

8. The process of claim 7 wherein said 1,2-dihaloethane is 1,2-dibromoethane.

9. The process of claim 8 wherein said promoter is hydrogen bromide.

* * * * *